United States Patent [19]

Ingle, Jr.

[11] 4,043,179
[45] Aug. 23, 1977

[54] NON-DESTRUCTIVE TESTING OF BONDING LAMINATES

[76] Inventor: Harold R. Ingle, Jr., 2665 Jamerson Road, NE., Marietta, Ga. 30066

[21] Appl. No.: 703,994

[22] Filed: July 9, 1976

[51] Int. Cl.² .............................................. G01N 29/00
[52] U.S. Cl. .......................................... 73/37; 73/67.2; 73/88 B
[58] Field of Search ...................... 73/37, 88 B, 150 A, 73/67.2

[56] References Cited

U.S. PATENT DOCUMENTS

| | | | |
|---|---|---|---|
| 2,512,134 | 6/1950 | Baule | 73/37 |
| 2,694,924 | 11/1954 | Matlock et al. | 73/37 |
| 3,564,903 | 2/1971 | Woodmansee et al. | 73/67.2 |

Primary Examiner—Jerry W. Myracle
Attorney, Agent, or Firm—Seidel, Gonda & Goldhammer

[57] ABSTRACT

A system responsive to pressure differential is provided for non-destructive testing of the bonding between a face sheet and the attached core of a laminated or like composited structure, including an internally evacuated transducer arranged to glide easily over the surface being scanned while maintaining a constant or pulsating vacuum. Displacement of the face sheet is detected by the transducer which generates a signal indicative of the extent of the defective bond.

15 Claims, 8 Drawing Figures

NON-DESTRUCTIVE TESTING OF BONDING LAMINATES

BACKGROUND OF THE INVENTION

Structural panels of comparatively light but rigid construction are known in which a low density core, generally of honey-combed or other cellular type material, is bonded at its upstanding edges defining the cells, to a face sheet on one or both sides of the core. Such structural panels have found wide use, for example, in the construction of aircraft wings, which undergo considerable stress in normal use. It is therefore important that a secure adhering bond be maintained between the face sheet and the core substantially over the entire area of the panel. Testing of the panels for locating bonding defects has at times been carried out manually by light tapping of local areas with a hammer for differences in sounding indicating to the experienced ear of the operator a loose area or defective bond.

It has been proposed to improve the described manual testing by applying to local areas of the panel an inverted bowl member associated with means for producing a vacuum between the inner surface of the bowl and the surface of the panel, so that the applied suction would lift the skin or face sheet of the panel at places where it was not properly bonded to the core. Means were provided for detecting any bulged areas. Such arrangement is disclosed, for example, in U.S. Pat. No. 2,694,924. Since the operation of this type of device necessitated that for effecting the desired suction, a hermetic seal be maintained at the rim of the bowl which defined the area being tested, considerable time was involved in making and then breaking the vacuum to enable the test apparatus to be moved over other areas of the panel to be tested.

Other types of transducer testing devices are known, such as those utilizing ultrasonic or other fault detecting means, which require elaborate systems for analyzing the received signal and for transforming the same to useful intelligence for evaluation, and requiring special skills for their operation. Most of the known transducer test instruments of these types depend upon the use of an impedance coupling liquid. Also, those that can be moved over a surface for scanning require the use of lubricants to reduce surface friction.

Summary of the Invention

Among the objects of the present invention are to provide a practical system for non-destructive testing of bonded structures, simple to use by operators, not requiring specialized skills, and in which faulty structures can be reliably and positively detected.

These objects are achieved, in accordance with the present invention, by provision of a vacuum-applying test instrument capable of being readily moved over a surface to be tested without necessitating repeated interruption of the vacuum. By the use of the device of the invention, the surface of a composite panel structure, having a face sheet bonded to a core, can be rapidly and continuously scanned and fault areas therein detected by an associated sensor. In accordance with preferred embodiments, the sensor means on physical contact with a fault area actuates an electrical transducer operatively arranged to activate a signal easily observable by the operator.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

DETAILED DESCRIPTION OF THE PREFERRED EMBODIMENTS

Figure 1:
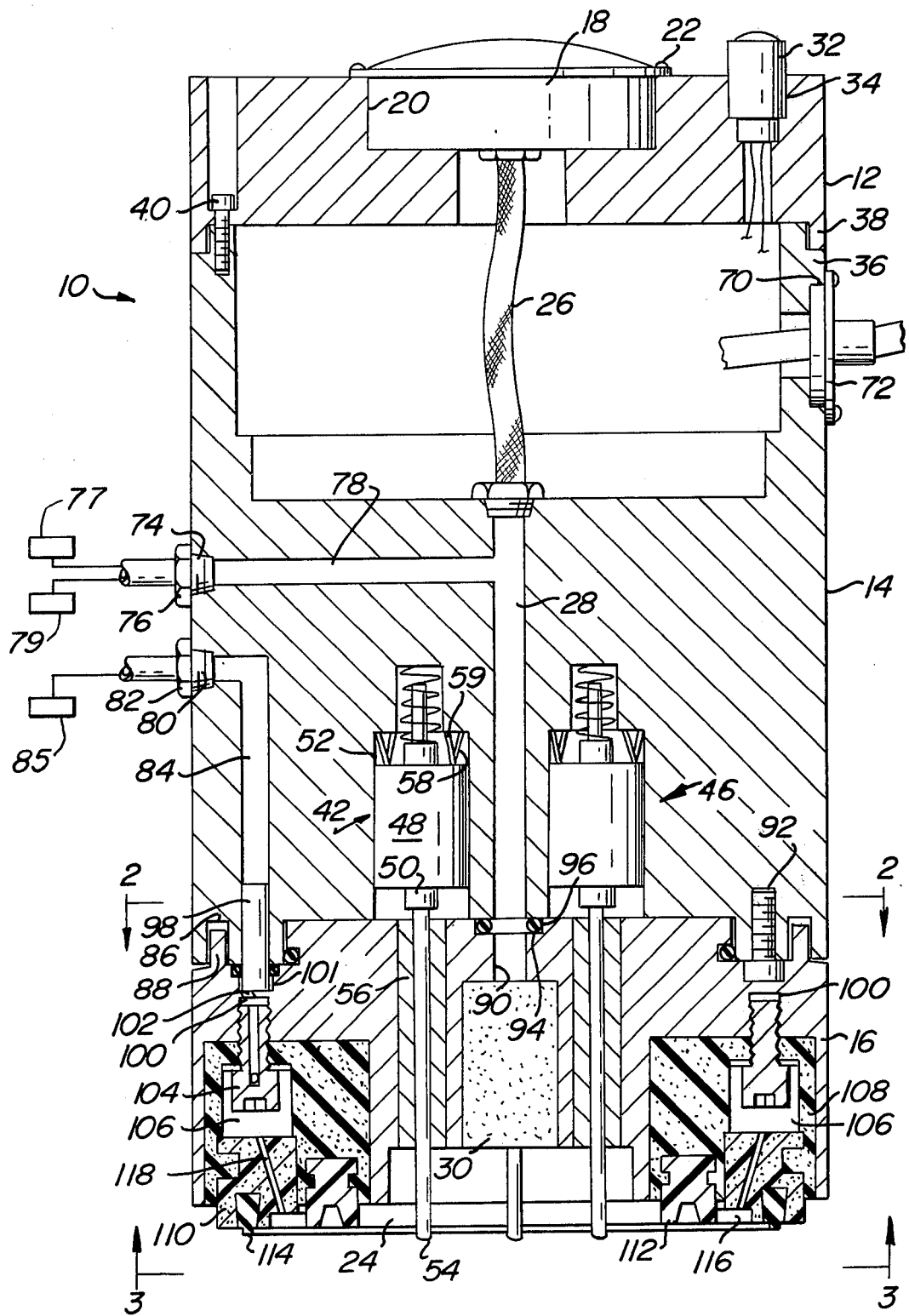
FIG. 1 is a longitudinal sectional view of the testing device of the present invention.

Referring to the drawings in detail wherein like numerals indicate like elements, there is shown in FIG. 1 a testing device 10 constructed in accordance with the principles of the present invention. Testing device 10 comprises an upper housing 12, a central housing 14 and a bottom housing 16.

A vacuum gauge 18 is housed in a recess 20 in upper housing 12 and is secured to housing 12 by appropriate fasteners 22. Vacuum gauge 18 is connected to vacuum chamber 24 in lower housing 16 via flexible conduit 26, bored channel 28 and porous air filter 30 and provides a visual indication of the quality of the vacuum in vacuum chamber 24. An indicator lamp 32 is also housed in a recess 34 in upper housing 12 and is electrically connected to a control circuit 200 described in detail below. Control circuit 200 energizes indicator lamp 32 whenever testing device 10 detects a fault area in the composite panel being tested which is greater than a predetermined permissible value.

An annular shelf 36 in central housing 14 supports a mating annular flange 38 in upper housing 12. Upper housing 12 is securely fastened to central housing 14 by a plurality of screws 40 which are reset into central housing 12 at a plurality of spaced locations about the periphery of upper housing 12.

Figure 2:
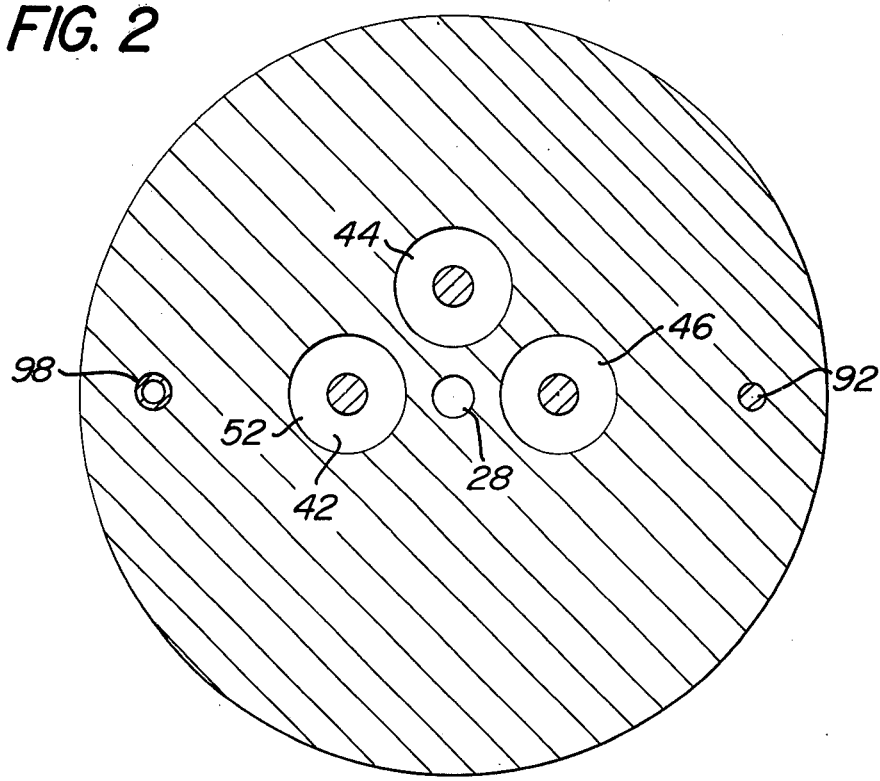
FIG. 2 is a transverse sectional view taken along line 2—2 of FIG. 1.
Figure 3:
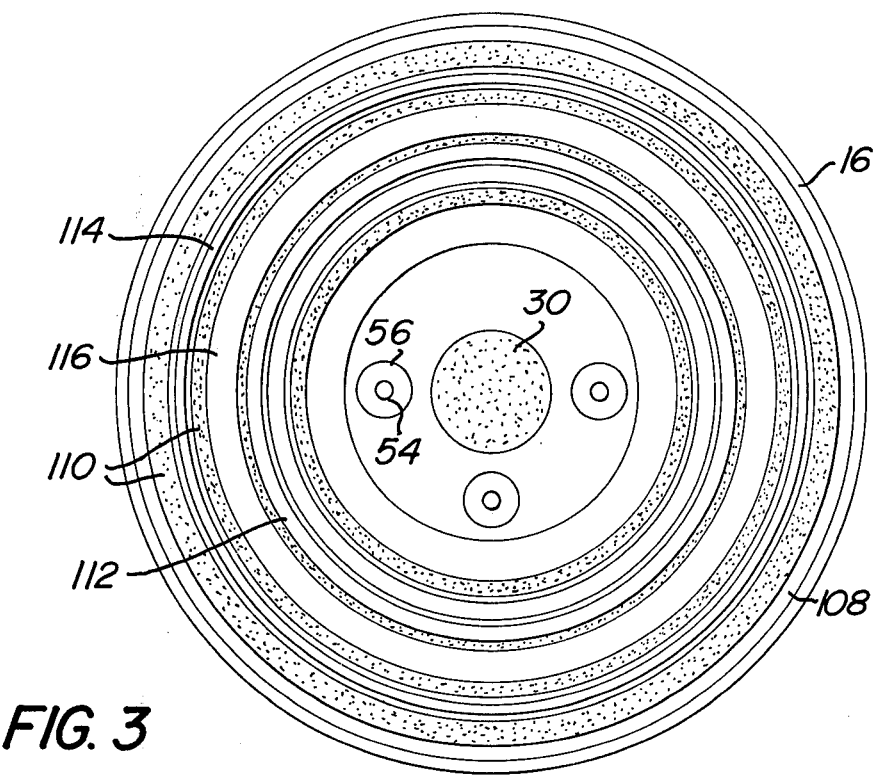
FIG. 3 is a transverse sectional view taken along line 3—3 of FIG. 1.

Embedded in central housing 14 are three linear variable differential transformers (LVDT's) 42, 44 and 46. See FIGS. 1 and 2. Each LVDT 42–46 is identical in its construction and operation. Accordingly, the following description of LVDT 42 is equally applicable to LDVTs 44 and 46.

LDVT 42 comprises a body portion 48 housing the primary and secondary windings of the transformer and a central core 50 which is slideably mounted within the LVDT body portion 48. Body portion 48 is forceably inserted into a cavity 52 in central housing 14 so that it will remain stationary with respect to central housing 14. Extending from core 50 of LVDT 42 is an elongated foot 54 which extends through bottom housing 16 and contacts the surface of the laminate being tested. A Thompson linear instrument bearing 56 surrounds a substantial portion of foot 54 and restricts movement of foot 54 to the axial direction.

Figure 5:
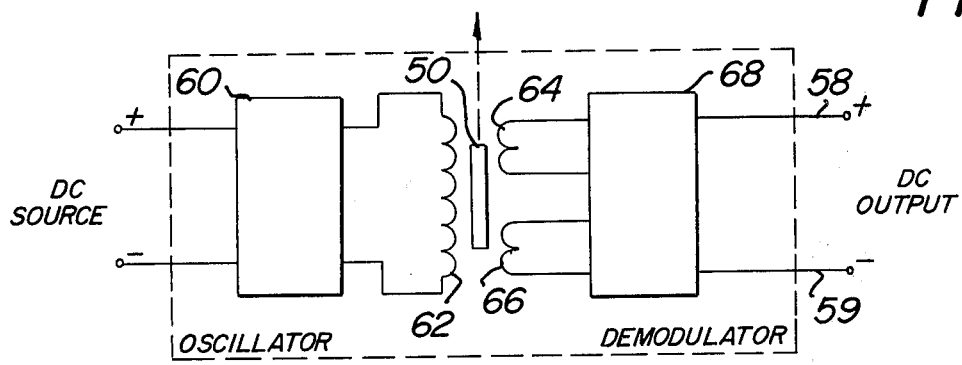
FIG. 5 is a schematic diagram of a transducer used in connection with the present invention.

LVDT 42 is a state of the art device which generates a D-C output on its output lines 58, 59 which is representative of the position of core 50 with respect to body portion 48. The operation of LVDT 42 can best be described with reference to FIG. 5. A D-C power source is connected across an oscillator 60 which alternately interrupts the current through either side of a center tapped primary winding 62. The resultant magnetic field induces a current in secondary windings 64 and 66 which is proportional to the position of core 50 with respect to windings 62–66. Each secondary winding 64, 66 is fed into a full wave bridge demodulator 68 whose D-C output on lines 58, 59 is representative of the position of core 50 with respect to windings 64–66. The LVDT is in the null position when core 50 is in the center of the LVDT body 48. In this position, the D-C voltage on output line 58 and output line 59 are of equal but opposite magnitudes. As core 50 moves upwardly in body portion 48 such that core 50 moves in the direction of secondary winding 64, the output line 58 becomes more positive and output line 59 becomes less negative. Conversely, when core 50 moves downwardly in body portion 48 such that core 50 moves in the direction of secondary winding 66, output line 58 becomes less positive and output line 59 becomes more negative. A commercially available LVDT which can be used with the present invention is manufactured by Pickering and Company, Inc., under the product designation 7304.

Referring again to FIG. 1, Central housing 14 is provided in the lateral wall thereof with a bore 70 which receives a connector 72. Connector 72 connects LVDTs 42–46 and indicator lamp 32 with external control circuit 200 (see FIGS. 4A and 4B and accompanying description below). An internally threaded bore 74, also located in the lateral wall of housing 14, receives a correspondingly threaded connector 76 which connects bored channel 78 to an external vacuum source 77. A similarly internally threaded bore 80 cooperates with an externally threaded connector 82 to connect bored channel 84 with an external compressed air pump.

An O ring 94 sits within a circumferential channel 96 in lower housing 16 and serves to preserve the integrity of the vacuum at the interface between bored channel 28 and bored channel 90.

An axially extending channel 86 in central housing 14 receives an axially extending flange 88 in lower housing 16 to assure concentricity of housings 14 and 16. Central housing 14 and lower housing 16 must be accurately align to assure continuity between bored passage 28 in central housing 14 and bored passage 90 in lower housing 16 as well as to avoid undue lateral forces on the feet extending from the cores of LVDTs 42–46. Lower housing 16 is tightly secured to central housing 14 by a plurality of bolts 92 located at spaced points around the periphery of lower housing 16.

The compressed air from a source 85 is pumped through bored channel 84 is delivered to an annular run 100 by a cylindrical sleeve 98 protruding from bored channel 84 into recess 101 in lower housing 16 and drilled passageway 102. A plurality of modified Allen screws 104 are provided at spaced intervals around the circumference of bottom housing 16 and distribute air from the annular run 100 into air distribution chamber 106.

Air distribution chamber 106 is an annular chamber cut into a silicon rubber ring 108 embedded in housing 16. Silicon rubber ring 108 supports a Teflon air bearing 110 and a Teflon vacuum seal 112. A silicon rubber seal 114 is embedded in air bearing 110 and is both sufficiently pliable to conform to subtle surface irregularities in the laminate being tested and to permit bleeding of compressed air in bearing recess 116 at the bottom of bottom housing 16. Compressed air enters bearing recess 16 through a plurality of drilled channels 118 in air bearing 110. While it is preferable to provide a pliable silicon rubber seal 114, testing device 10 will operate satisfactorily using only air bearing 110.

Vacuum seal 112 serves the dual purpose of maintaining a vacuum in vacuum chamber 24 and maintaining a chamber of highly compressed air in bearing recess 116. While the exact proportion between the compressed air in bearing recess 116 and the vacuum in vacuum chamber 24 will vary for different applications, the ratio should be sufficient to permit easy movement of testing device 10 along the outer surface of the laminate being tested while at the same time not breaking the vacuum in vacuum chamber 24.

Figure 6:
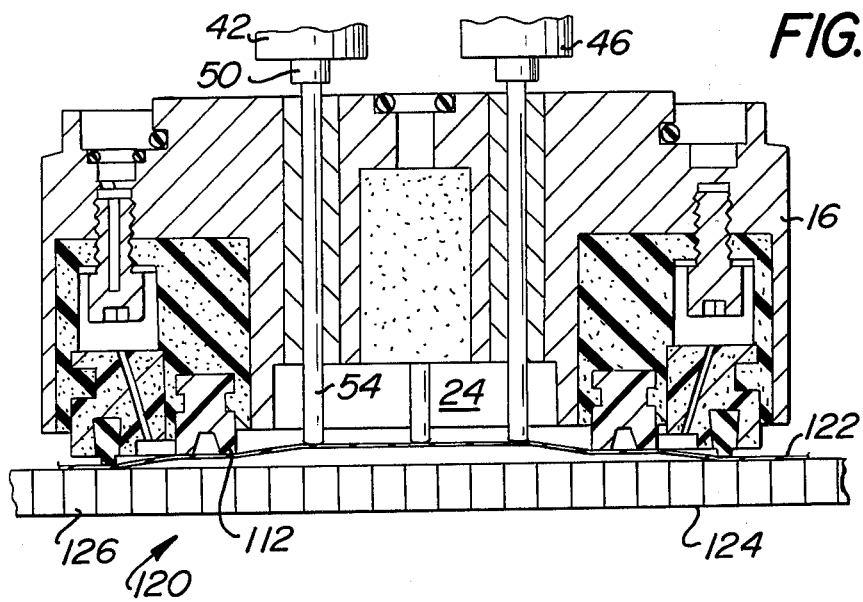
FIG. 6 is a partial cross-sectional view of the testing device of the present invention in operating position over part of a panel being tested.

Referring now to FIG. 6, testing apparatus 10 is shown in its operating position with respect to composite panel 120. The composite panel 120 illustrated in FIG. 6 is an airplane wing having an upper face sheet 122 and a lower cover sheet 124 sandwiching therebetween a cellular core 126. Sheets 122 and 124 are bonded to the upper and lower edges, respectively, of cellular core 126. While an airplane wing is illustrated, the present invention may be used with other composite panels whose surface sheet is bonded to a central core.

In the section of composite panel 120 illustrated in FIG. 6, upper face sheet 122 has detached from core 126 and has been pulled up into vacuum chamber 24. The displacement in face sheet 122 results in a similar displacement in the feet of LVDTs 42–46 and cause the output of LVDTs 42–46 to change. This change is detected by control circuit 200 which will energize indicator lamp 32 if the deflection of upper face sheet 122 is greater than some predetermined maximum value.

Figure 4A:
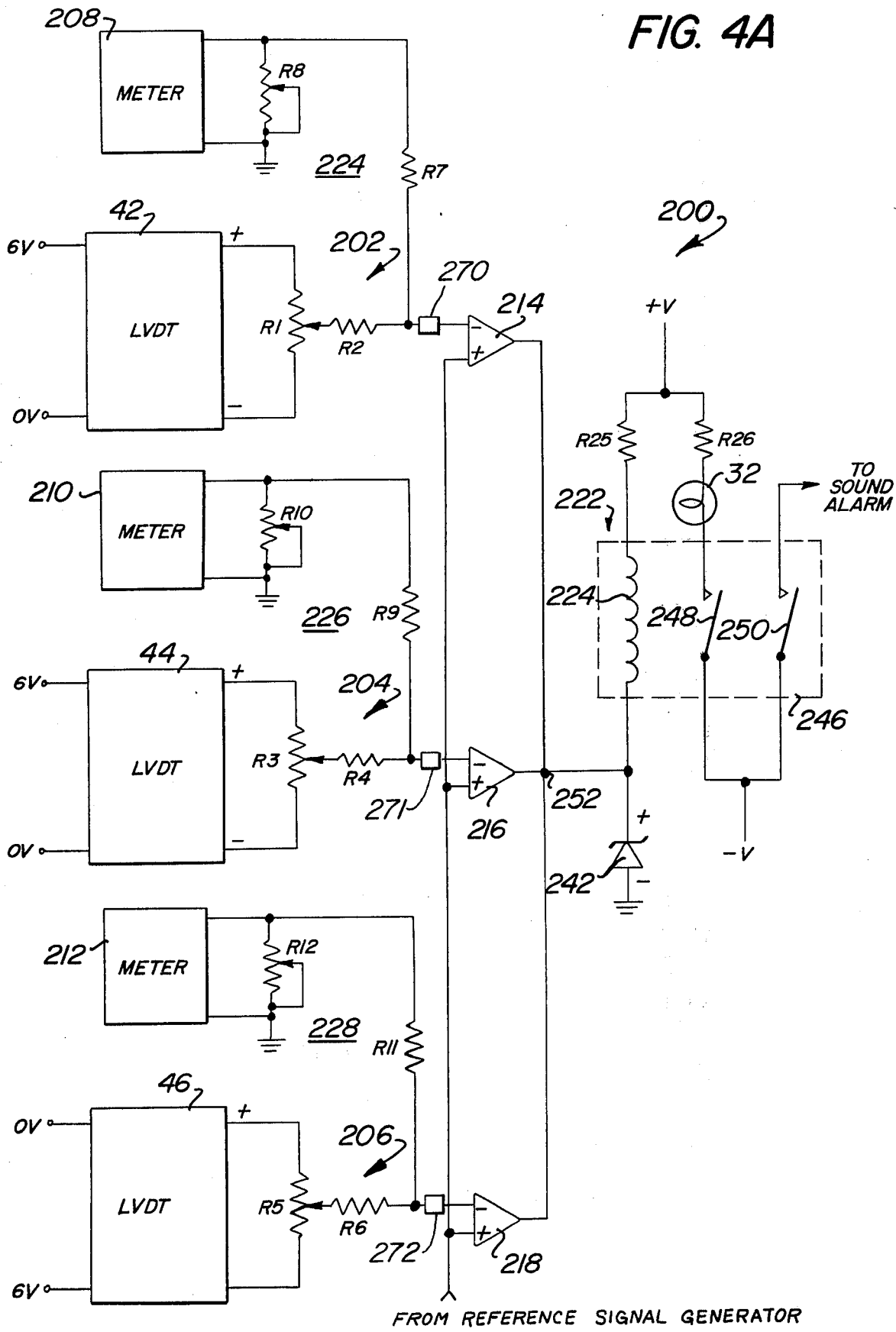
FIG. 4a is a schematic diagram of a portion of the control circuit of the present invention.
Figure 4B:
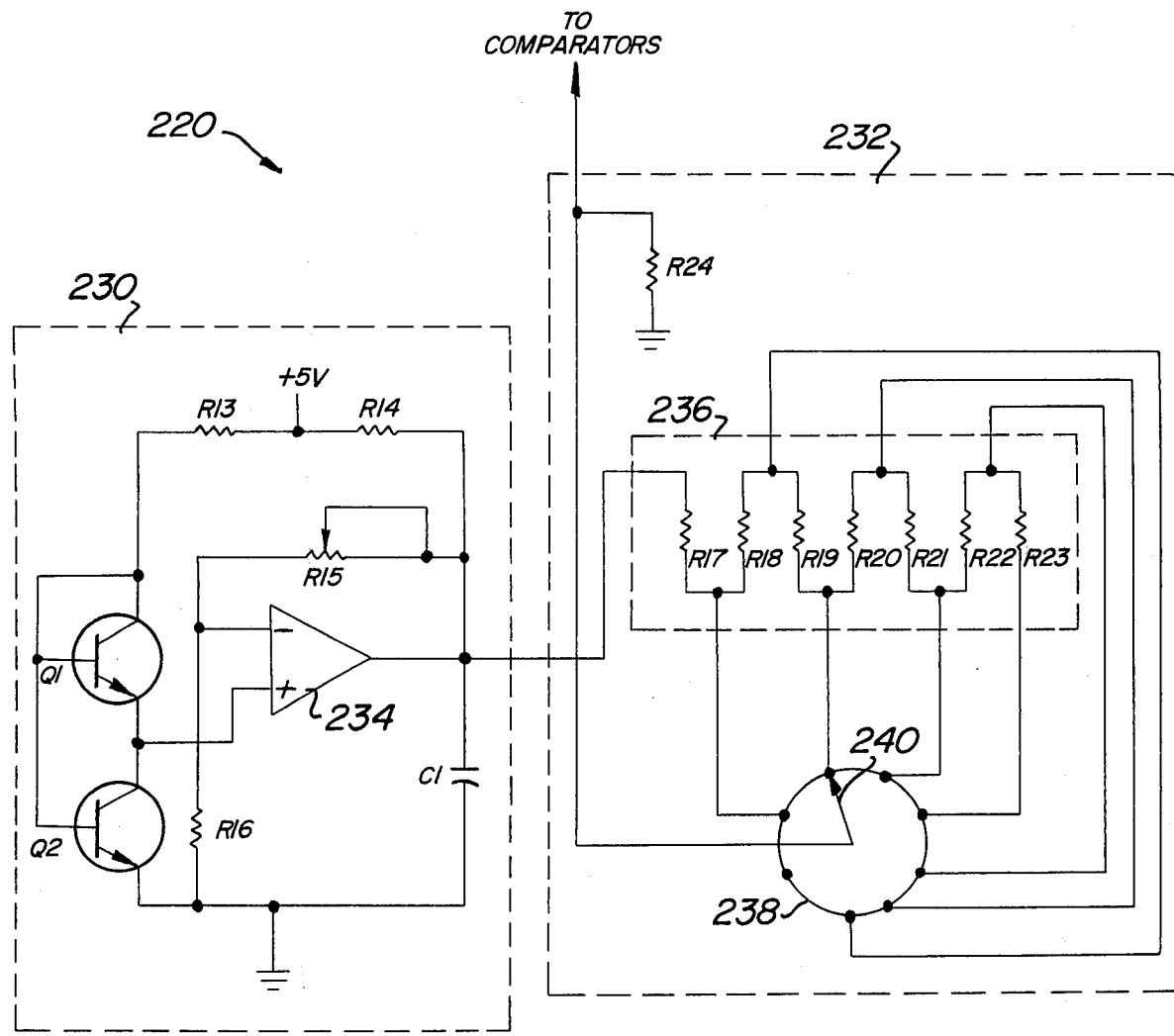
FIG. 4b is a schematic diagram of a portion of the control circuit of the present invention.

Referring now to FIGS. 4a and 4b, control circuit 200 comprises nulling circuits 202, 204 and 206, digital meters 208, 210 and 212, comparators 214, 216 and 218, reference signal generator 220 and relay 222. Control circuit 200 provides three functions. Initially, control circuit 200 adjusts the output of LVDTs 42–46 so that their output will be 0 volts D-C when testing device 10 is in operative contact with the laminate being tested and there is zero displacement of the upper face sheet of the laminate with respect to the core of the laminate. Control circuit 200 also provides a continuous visual indication of the actual instantaneous deflection of the top face sheet of the laminate with respect to the laminate core. Finally, circuit 200 continually monitors the displacement of the face sheet of the laminate and enables indicator lamp 32 whenever the displacement of the face sheet exceeds a predetermined permissible value set by reference signal generator circuit 220.

The output of LVDTs 42, 44 and 46 are applied to the inverting input comparators 214, 216 and 218, respectively, via nulling circuits 202, 204 and 206. Nulling circuit 202 comprises potentiometer R-1 and resistor R-2. Nulling circuit 204 comprises potentiometer R-3 and resistor R-4. Nulling circuit 206 comprises potentiometer R-5 and resistor R-6. By properly adjusting the slide arm of potentiometers R-1, R-3 and R-5, it is possible to apply an input voltage of 0 volts D-C to the inverting terminals of comparators 214, 216 and 218 whenever there is zero displacement of the outer face sheet of the composite panel being tested. After the slide arm of potentiometers R-1, R-3 and R-5 have been so adjusted, the voltage at the slide arms will be directly proportional to the displacement of the foot of its respetive LVDT and will therefore be proportional to the displacement of the face sheet of the panel being tested.

The voltage at the output of nulling circuits 202, 204 and 206 is applied to meters 210, 212 and 214, respectively, via scaling circuits 224, 226 and 228. Scaling circuit 224 comprises fixed resistors R-2 and R-7 and variable resistor R-8. Scaling circuit 226 comprises fixed resistors R-4 and R-9 and variable resistor R-10. Scaling circuit 228 comprises fixed resistors R-6 and R-11 and variable resistor R-12. By appropriately adjusting variable resistors R-8, R-10 and R-12, it is possible to calibrate meters 208, 210 and 212 so that the meters read directly in thousands of an inch. A suitable digital meter is manufactured by Analog Devices under the product designation AD2003.

Comparators 214, 216 and 218 are analog devices whose output is at its positive saturation value +Vsat when its non-inverting input terminal is at a greater value than its inverting input terminal and whose output is at a maximum negative saturation value −Vsat when its inverting input terminal is at a greater value than its non-inverting input terminal. As noted above, the inverting input terminals of comparators 214, 216 and 218 are connected to the slide arm of potentiometers R-1, R-3 via resistors R-2, R-4 and R-6, respectively. The non-inverting input terminal comparators 214, 216 and 218 are connected to the output of reference signal generator 220.

Reference signal generator 220 (FIG. 4b) comprises voltage source 230 and voltage divider network 232. Voltage source 230 comprises operational amplifier 234, transistors Q-1 and Q-2 and resistors R-13, R-14, R-15 and R-16. Operational amplifier 234 is connected to operate as a difference amplifier and generates a D-C signal on its output which is proportional to the difference between the voltages applied to its inverting and non-inverting terminals. By appropriately adjusting the slide arm of adjustable resistor R-15, it is possible to accurately control the magnitude of the output of operational amplifier 234 and therefore the output of voltage source 230.

Voltage divider network 232 comprises resistor network 236 and eight position wafer switch 238. The output of voltage source 230 is applied to the input of resistor network 236 which comprises resistors R-17 through R-23. Wafer switch 238 selectively connects resistor R-24 and the non-inverting terminals of comparators 214-218 to one of seven possible points in resistor network 236. By appropriately setting wiper arm 240, it is possible to place a desired number of consecutive resistors R-17 through R-23 in series with resistor R-24 and therefore to determine the fraction of the voltage generated by voltage source 230 which will be applied to the non-inverting terminals of comparators 214-218. Thus, in the position shown in FIG. 4b, wafer switch 238 places resistors R-17, R-18 and R-19 in series with resistor R-24 permitting a comparatively large portion of the voltage generated by voltage source 230 to be applied to comparators 214-218. If wiper arm 240 was rotated two positions to the right so that the entire resistor network 236 is placed in parallel with resistor R-24, a comparatively small portion of the voltage generated by voltage source 230 would be applied to comparators 214-218.

It should be apparent from the foregoing that the magnitude of the voltage applied to the non-inverting terminals of comparators 214-218 is grossly adjusted by properly setting the wiper arm 240 of wafer switch 236 and is finely adjusted by adjusting the slide arm of adjustable resistor R-15. As noted above, the voltage applied to the non-inverting terminals of comparators 214-218 determines the permissible deflection of the upper face sheet of the composite panel being tested. Accordingly, this value may be set by adjusting wafer switch 238 and resistor R-15.

As long as the deflection of the upper face sheet of the panel being tested is below the maximum permissible value set by reference signal generator 220, the output of comparators 214-218 will all be at their positive saturation value +Vsat. This voltage is applied to the cathode of zener diode 242, which is chosen such that the voltage at its cathode is equal to the voltage +V applied to resistor R-25 whenever the zener diode 242 is reversed biased. Accordingly, when the outputs of all three comparators 214-218 are at the positive saturable value +Vsat, no current flows through coil 244 of relay 246 and normally open switches 248 and 250 remain open. In this condition, both indicator lamp 32 and an external sound alarm (not shown) are disabled.

When testing device 10 is drawn across a portion of the composite panel being tested whose upper face sheet deflects an amount greater than the preset permissible amount, the output of at least one of the three LVDTs 42, 44 and 46 exceeds the output of reference signal generator 220 and the output of the associated comparator 214, 216 or 218 jumps to its negative saturation value −Vsat. Since the output of comparators 214-218 perform an OR function, summing junction 252 jumps to the negative saturation value −Vsat and zener diode 242 is forward biased. Current flows through relay 246 and normally open switches 248 and 250 are closed enabling both indicator lamp and an external sound alarm.

In the foregoing description of testing device 10, a constant vacuum is applied to vacuum chamber 24. While this embodiment is desirable in most applications of the invention, it will not operate satisfactorily when permissible tolerances are reduced to very small values for example 0.0012 inches. In these situations, testing device 10 will sometimes produce false fault signals due to natural imperfections in the surface of the composite panel being tested.

Figure 7:
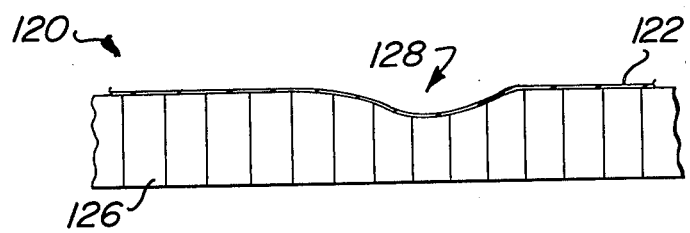
FIG. 7 is a cross-sectional view of a composite panel.

As shown in FIG. 7, normal surface irregularities such as dip 128 occur randomly in composite panel 120. If the dip is at least equal in magnitude to the maximum permissible defect in the panel 120, control circuit 200 will enable indicator lamp 32 and indicate an unacceptable fault in the composite panel. Such an indication is undesirable since the dip 128 does not represent a portion of face sheet 122 which has detached from core 126 but only represents a permissible imperfection in the composite panel. To avoid such problems, a second embodiment of the invention utilizes a pulsating vacuum to vibrate the panel being tested at some predetermined frequency. As will be shown below, this embodiment is responsive to changes in resonant frequency of composite plate 126 and not to absolute displacement of face sheet 122.

The pulsating vacuum is generated by any conventional source 79. The vacuum is applied via channels 28 and 78 to vacuum chamber 24 and causes composite plate 120 to vibrate at some predetermined frequency. As long as testing device is drawn over a portion of face sheet 122 which is properly bonded to core 126, the plate 120 will resonate at the predetermined frequency regardless of any dips or rises in composite plate 120. When testing device 10 is drawn over a portion of face sheet 120 which has partially detached from core 126, the resonance characteristics of the composite plate change and the face sheet 122 vibrates at a frequency different from the predetermined resonant frequency of the properly bonded areas. The magnitude of this frequency change is proportional to the size of the portion of face sheet 122 which has dislodged from core 126.

Since the feet extending from the cores of LVDTs 42-48 are in constant contact with the face sheet, the output of the LVDTs has a frequency representative of the instanteous resonant frequency of the face sheet. A Phase Locked Loop (PLL) is utilized to detect the frequency change in the output of LVDTs 42-46. One PLL 270, 271, 272 is interposed between the output of each LVDT and the inverting input terminal of its associated comparator. PLL's 270, 217, and 272 shown in FIG. 4A are utilized only when a pulsating vacuum is used and not when the constant vacuum is used. A suitable PLL is the 565 Phase Locked Loop manufactured by Signetics Corporation. This PLL has a comparator at its output and generates a D-C voltage which is proportional to the difference between a reference frequency and a new frequency coming into the PLL.

The frequency of the pulsating vacuum applied to vacuum chamber 24 is adjusted to match the particular resonant frequency of the laminate being tested which will provide a large frequency change when the testing device is drawn over a defect area in the laminate. The PLL will detect deviation from this value and generates a D-C voltage at its output which is representative of the magnitude of the change. The size of the permissible defect is again determined by reference signal generator 220 which applies a voltage signal to the non-inverting inputs of comparators 214 through 218. As long as the change in the output of the LVDT (and therefore the size of the defect in the laminate) remains below the predetermined value set by the reference signal generator 220, relay 222 is disabled and indicator lamp 32 is off. When the change in the output of any of the LVDTs surpasses the predetermined value, relay 222 is energized and indicator lamp 32 is enabled to indicate that a fault area has been traversed.

The present invention may be embodied in other specific forms without departing from the spirit or essential attributes thereof and, accordingly, reference should be made to the appended claims, rather than to the foregoing specification as indicating the scope of the invention.

What is claimed is:

1. Apparatus for non-destructive tested of bonded laminates which include a substrate and a face sheet bonded thereto, comprising:
   a vacuum chamber adapted to contact the surface of said face sheet as said apparatus is drawn across said face sheet;
   means for applying a vacuum to said vacuum chamber thereby urging said face sheet into said vacuum chamber;
   compressed air means for counteracting the normal force of said vacuum with respect to said face sheet to permit said apparatus to be drawn across said face sheet while said vacuum is maintained in said vacuum chamber; and
   means for detecting the magnitude of the displacement of said face sheet into said chamber.

2. Apparatus in accordance with claim 1 wherein said conventional air means comprises an annular channel surrounding said vacuum chamber and means for applying compressd air to said annular channel.

3. Apparatus in accordance with claim 2 wherein the ratio between the normal force applied by said vacuum in said vacuum chamber to said face sheet and the normal force applied by said compressed air in said annular channel to said face sheet is such that said apparatus may be easily traversed over said composite plate while at the same time said vacuum is maintained in said vacuum chamber.

4. Apparatus in accordance with claim 2 wherein said vacuum chamber is defined in part by an annular, resilient vacuum seal and wherein said annular recess is defined in part by said vacuum seal and a concentric annular seal of greater diameter than said vacuum seal.

5. Apparatus in accordance with claim 1 including means for indicating that said face sheet has been displaced an amount greater than some predetermined permissible displacement.

6. Apparatus in accordance with claim 1 including means for continuously indicating the magnitude of the displacement of said face sheet.

7. Apparatus in accordance with claim 1 wherein said means for detecting the magnitude of the displacement of said face sheet comprises:
   transducer means in operative contact with said face sheet for generating a D-C signal representative of the displacement of said face sheet; and
   circuit means responsive to said D-C signal for enabling an indicator means when the displacement of the face sheet is greater than some predetermined value.

8. Apparatus in accordance with claim 7 wherein said circuit means comprises:
   means for generating a reference signal representative of the predetermined amount of permissible displacement of the face sheet;
   comparator means for generating an enabling signal when the displacement of said face sheet exceeds said predetermined value; and
   means responsive to said enabling signal for enabling said indicator means.

9. Apparatus for non-destructive testing of bonded laminates which include a substrate and a face sheet bonded thereto, comprising:
   a vacuum chamber adapted to contact the surface of said face sheet as said apparatus is drawn across said face sheet;
   means for applying a pulsating vacuum to said vacuum chamber thereby resonating said face sheet at some predetermined frequency,
   means for counteractng the normal force of said vacum with respect to said face sheet to permit said apparatus to be drawn across said face sheet while said vacuum is maintained in said vacuum chamber; and
   means for detecting changes in the resonant frequency of said face sheet.

10. Apparatus in accordance with claim 9 wherein said means for counteracting the normal force of said vacuum comprises an annular channel surrounding said vacuum and means for applying compressed air to said annular channel.

11. Apparatus in accordance with claim 10 wherein the ratio between the normal force applied to said vacuum in said vacuum chamber to said face sheet and the normal force applied by said compressed air in said annular channel to said face sheet is such that the apparatus may be easily traversed over said composite plate while at the same time said vacuum is maintained in said vacuum chamber.

12. Apparatus in accordance with claim 10 wherein said vacuum chamber is defined in part by an annular, resilient vacuum seal and wherein said annular recess is defined in part by said vacuum seal and a concentric annular seal of greater diameter than said vacuum seal.

13. Apparatus in accordance with claim 9 including means for indicating that the vibrational frequency of said face sheet has changed an amount greater than some predetermined permissible value.

14. Apparatus in accordance with claim 9 wherein said means for detecting changes in the vibrational frequency of said face sheet comprises:
- transducer means in operative contact with said face sheet for generating a signal representative of the displacement of said face sheet; and
- circuit means responsive to said signal for enabling an indicator means when the change in the vibrational frequency of said face sheet is greater than some predetermined value.

15. Apparatus in accordance with claim 14 wherein said circuit means comprises:
- means for generating a reference signal representative of the predetermined amount of permissible change in the vibrational frequency of said face sheet;
- means for generating a signal representative of the change in the vibrational frequency of the face sheet;
- comparator means for generating an ensabling signal when the change in the vibrational frequency of said face sheet exceeds said predetermined value; and
- means responsive to said enabling signal for enabling said indicator means.

* * * * *